United States Patent [19]
Rrbczynski et al.

[11] Patent Number: 5,514,806
[45] Date of Patent: May 7, 1996

[54] METHOD OF PREPARING 1-AMINO-2,6-DIMETHYLPIPERIDINE

[75] Inventors: Wolfgang Rrbczynski, Rodenbach; Manfred Schrod, Weiterstadt, both of Germany

[73] Assignee: Cassella Aktiengesellschaft, Frankfurt am Main, Germany

[21] Appl. No.: 244,134
[22] PCT Filed: Nov. 12, 1992
[86] PCT No.: PCT/EP92/02593
§ 371 Date: May 17, 1994
§ 102(e) Date: May 17, 1994
[87] PCT Pub. No.: WO93/10109
PCT Pub. Date: May 27, 1993

[30] Foreign Application Priority Data

Nov. 20, 1991 [DE] Germany .................. 41 38 142.4

[51] Int. Cl.$^6$ .................. C07D 211/98
[52] U.S. Cl. .................. 546/244
[58] Field of Search .................. 546/244

[56] References Cited

U.S. PATENT DOCUMENTS 2,979,505  4/1961  Tuemmler et al. .................. 260/247.5

Primary Examiner—C. Warren Ivy
Assistant Examiner—Raymond Covington
Attorney, Agent, or Firm—Perman & Green

[57] ABSTRACT

The present invention relates to improved processes for the preparation of 1-amino-2,6-dimethylpiperidine whereby the yield is more than 90%. The processes involve the hydrogenation of 1-nitroso-2,6-dimethylpiperidine in the presence of a palladium catalyst partly poisoned with iron ions but in the substantial absence of water or other solubilizing agents added to the reaction vessel.

14 Claims, No Drawings

METHOD OF PREPARING 1-AMINO-2,6-DIMETHYLPIPERIDINE

The invention relates to a process for the preparation of 1-amino-2,6-dimethylpiperidine.

1-Amino-cis-2,6-dimethylpiperidine is a key intermediate product in the synthesis of the loop saluretic clopamide (4-chloro-N-(cis-2,6-dimethylpiperidino-sulfamoylbenzamide) and the cardiovascular agent pirsidomine (3-(cis-2,6-dimethylpiperidino)-N-(4-methoxybenzoyl)-sydnonimine).

All the known preparation processes for 1-amino-2,6-dimethylpiperidine are based on reduction of 1-nitro-so-2,6-dimethylpiperidine. All show an incomplete conversion and above all ecological deficiencies.

Furthermore, the production of large amounts of waste salts in the reduction with sodium dithionite (C.G. Overberger, J.G. Lombardino and R.G. Hiskey, J. Org. Chem. 22 (1957) 858) is a disadvantage.

The use of zinc in dilute acetic acid as the reducing agent (E. Jucker and A. Lindamann, Helv. Chim. Acta, 45 (1962) 2316–2325, in particular 2323) leads to a considerable heavy metal pollution of the resulting waste water.

Reduction with complex hydrides, such as lithium aluminum hydride in ether (C.G. Overberger, L.C. Palmer, S.S. Marks and N.R. Byrd, J. Am. Cham. Soc. 77 (1955) 4100) or bis(2-methoxyethoxy)-sodium aluminum hydride in toluene (M. Londyn and M. Borovicka, Czechoslovakian Patent 253243, applied for on 21.01.1986) cannot be carried out on a larger scale for safety reasons. A process is known from U.S. Pat. No. 2,979,505 for the preparation of substituted hydrazines, such as, for example, N-aminopiperidine, in which the corresponding nitrosamines are hydrogenated in the presence of a palladium catalyst which contains a certain amount of a soluble iron salt. The hydrogenation of heterocyclic nitrosamines, such as, for example, of nitrosopiperidine, by this process is carried out in aqueous or ethanolic solution.

According to Hungarian Patent 15614, the preparation of 1-amino-cis-2,6-dimethylpiperidine by this process is unsatisfactory both in respect of the yield (65%) and in respect of the selectivity (60 to 70%). According to the process of Hungarian Patent 15614, 1-amino-cis-2,6-dimethylpiperidine is therefore prepared by nitrosation of cis-2,6-dimethylpiperidine and hydrogenation of the resulting nitroso compound in aqueous ammoniacal solution in the presence of a palladium catalyst partly poisoned with an Fe(II) salt, the two reactions being carried out in the absence of chloride ions. This process shows considerable problems both in the reaction and in the working-up of the reaction mixture obtained. Thus, for example, the use of ammonia requires additional process technology measures to avoid corrosion and emission. Furthermore, the amount of ammonia used is high (100 to 150 g of ammonia per kg of product). The incomplete conversion, which causes the product to contain still unreacted 1-nitroso-2,6-dimethylpiperidine, is, as in the other processes, a disadvantage. In the process of Hungarian Patent 15614, it is still at least 3%. Nevertheless, the main difficulty is the large amount of water in the reaction mixture, which is caused by the process and makes isolation of the product very much more difficult.

During subsequent rectification, the product and by-product (cis-2,6-dimethylpiperidine) pass over together with water (as a rule at 85° to 95° C./atmospheric pressure), so that there is the prospect of isolation of the product only if extremely expensive columns are employed. Only multistage extractor processes remain as alternatives for isolation of the product. The organic solvents used here require increased safety measures and treatment of the waste water and waste air. To remove the relatively strongly basic by-product 2,6-dimethylpiperidine the addition of a corresponding amount of acid substances is necessary, which means that the waste water is polluted even more (M. Londyn, Czechoslovakian Patent 253898).

The object of the present invention was therefore to provide a process for the preparation of 1-amino-2,6-dimethylpiperidine by reduction of 1-nitroso-2,6-dimethylpiperidine which does not have the disadvantages of the processes which have been disclosed to date and by which, in particular, a complete conversion is achieved.

The invention thus relates to a process for the preparation of 1-amino-2,6-dimethylpiperidine by catalytic hydrogenation of 1-nitroso-2,6-dimethylpiperidine using a palladium catalyst partly poisoned with iron ions. The process according to the invention is characterized in that it is carried out without initial introduction of a solvent and a solubilizing agent into the reaction vessel.

In carrying out the process according to the invention, only the palladium catalyst partly poisoned with iron ions and the starting substance 1-nitroso-2,6-dimethylpiperidine are employed in the hydrogenation.

The palladium catalyst is preferably employed in an amount such that the amount of Pd is 0.1 to 10 mol%, based on the 1-nitroso-2,6-dimethylpiperidine.

The palladium catalysts used are, in particular, those in which the palladium is adsorbed onto a support, preferably charcoal or aluminum oxide, and which have a Pd content of 1 to 10% by weight.

The catalyst is partly poisoned by addition of a soluble iron salt before the reaction. Fe(II) sulfate is particularly suitable as the soluble iron salt here. The molar ratio of Pd:Fe is preferably (20 to 0.5):1. The partial poisoning of the palladium catalyst can be carried out, for example, by stirring the catalyst and the iron salt in water, expediently under an inert gas, for about 10 to 120 minutes. The partly poisoned palladium catalyst is then separated off, for example filtered off with suction or filtered off, and if appropriate dried by suction or other means. However, it can also be employed in the moist form.

The hydrogenation is carried out at normal temperature or preferably at elevated temperature, for example at 20° to 80° C., and, for example, under a hydrogen pressure of 1 to 100 bar. A reaction temperature of 30° to 50° C. and/or a hydrogen pressure of 2 to 25 bar is particularly preferred here.

Surprisingly, a practically complete conversion of more than 99% is achieved by the process according to the invention. The starting substance 1-nitroso-2,6-dimethylpiperidine used is detectable in the reaction product, if at all, only in traces using sensitive detection methods.

The reaction mixture which remains in the process according to the invention after the catalyst has been filtered off can be worked up, for example, by rectification. The rectification can be carried out in the range from 20 mbar to atmospheric pressure. Vacua in the range from 50 to 300 mbar are preferred here. The top product comprises 2,6-dimethylpiperidine and water. This mixture can be re-used in the preparation of 1-nitroso-2,6-dimethylpiperidine. The bottom product which remains comprises 1-amino-2-6-dimethylpiperidine to the extent of more than 99% and can be passed in this form to the synthesis of the medicaments mentioned at the outset. The boiling points of the top product and bottom product are 40 to 50 degrees apart, so that a simple column is adequate for isolation of the products.

If the remaining traces of impurities (for example 1-nitroso-2,6-dimethylpiperidine) are likewise to be removed from the product, this can be effected by further rectification, the 1-amino-2,6-dimethylpiperidine being collected as the second fraction.

The process according to the invention is equally suitable for the preparation of 1-amino-cis-2,6- or -trans-2,6-dimethylpiperidine.

Compared with the known preparation processes, the process according to the invention offers several considerable advantages. Thus, for example, isolation of the products is drastically simplified. In the reaction, the 1-nitroso-2,6-dimethylpiperidine employed is reacted to the extent of more than 99%, that is to say practically completely, with a simultaneously high selectivity of more than 90%, it being possible for the selectivity to be increased further by recycling the by-product. The volume yield is high (up to, for example, 500 g/l of autoclave volume). Since only small amounts of water are required for the pretreatment of the catalyst and the cleaning of the apparatus, a drastic reduction in the amount of waste water is achieved by the process according to the invention. Organic solvents and solubilizing agents, such as ammonia, are avoided completely. Additional process technology measures are thereby also eliminated completely, and safety is improved. Because of the few process steps, a high space/time yield and a significant saving in energy also result.

EXAMPLE 20 g of a Pd catalyst absorbed onto A charcoal and having a Pd content of 10% by weight and 5 g of $FeSO_4 \times 7\ H_2O$ are stirred in 100 ml of distilled water under a nitrogen atmosphere for 1 hour. The catalyst is then filtered off over a filter paper and sucked dry. The adhering moisture makes up about 50% by weight.

A 1 l autoclave is charged with this catalyst paste and 284 g of 1-nitroso-cis-2,6-dimethylpiperidine. At 40° C. and under a hydrogen pressure of 6 bar, the hydrogenation is finished after 12 hours.

After the catalyst has been filtered off, the reaction mixture contains more than 90% of 1-amino-cis-2,6-dimethylpiperidine, 9% by weight of cis-2,6-dimethylpiperidine and 1-nitroso-cis-2,6-dimethylpiperidine in traces which are only detectable by gas chromatography (conversion >99%; selectivity=90%). 50 to 60 ml of water are also obtained in this hydrogenation. This is composed of the residual moisture of the catalyst and the water of reaction formed. (The concentrations of product and by-product can be determined side by side by titration with dilute hydrochloric acid, but preferably by means of gas chromatography.)

The reaction is followed by rectification over a Kerapack column under 100 mbar. The by-product cis-2,6-dimethylpiperidine passes over together with the water at 39° to 43° C. and the product 1-amino-cis-2,6-dimethylpiperidine passes over at 90° to 96° C.

We claim:

1. In the process for the preparation of 1-amino-2,6-dimethylpiperidine by catalytic hydrogenation of 1-nitroso-2,6-dimentylpiperidine in the presence of a palladium catalyst partly poisoned with iron ions, the improvement which comprises increasing the yield to more than 90% by adding to a reaction vessel a reaction mixture consisting essentially of the 1-nitroso-2,6-dimethylpiperidine, said palladium catalyst and hydrogen gas, in the substantial absence of water or other solubilizing agents, and subjecting the reaction mixture to hydrogenation conditions to produce 1-amino-2,6-dimethylpiperidine in a yield of more than 90%.

2. Process according to claim 1, characterized in that the palladium catalyst is used in an amount such that the amount of Pd is 0.1 to 10 mol %, based on the 1-nitroso-2,6-dimethylpiperidine.

3. Process according to claim 1, characterized in that a Pd-supported catalyst, having a Pd content of 1 to 10% by weight is employed.

4. Process according to claim 1, in which the ratio of Pd:Fe is (20 to 0.5):1.

5. Process according to claim 1, in which 1-nitroso-cis-2,6-dimethylpiperidine is employed as the starting reactant.

6. Process according to claim 1, in which the hydrogenation is carried out at a temperature of 20° to 80° C.

7. Process according to claim 1, in which the hydrogenation is carried out under a hydrogen pressure of 1 to 100 bar.

8. Process according to claims 1, in which when the hydrogenation reaction is completed, the catalyst is separated off and the reaction is rectified.

9. Process according to claim 8, characterized in that the reaction is separated into aqueous 2,6-dimethylpiperidine and 1-amino-2,6-dimethylpiperidine during the rectification.

10. Process according to claim 9, characterized in that the aqueous 2,6-dimethylpiperidine which has been separated off is re-used to produce 1-nitrosa-2,6-dimethylpiperdine.

11. Process according to claim 6 in which the temperature is between 30° and 50° C.

12. Process according to claim 7 in which the hydrogen pressure is between 2 and 25 bar.

13. Process according to claim 3 in which the supported catalyst is a Pd/C catalyst.

14. Process according to claim 3 in which the supported catalyst is a $Pd/Al_2O_3$ catalyst.

* * * * *

UNITED STATES PATENT AND TRADEMARK OFFICE
CERTIFICATE OF CORRECTION

PATENT NO. : 5,514,806
DATED : 05/07/96
INVENTOR(S) : Wolfgang Rybczynski and Manfred Schrod It is certified that error appears in the above-identified patent and that said Letters Patent is hereby corrected as shown below:

Title page , item [75], the name "Rrbczynski" should read --Rybczynski--.

Col. 4, line 33, Claim 8, line 1, "claims" should read --claim--;

Col. 4, line 41, Claim 10, line 3, "1-nitrosa-2,6-dimethylpiperdine" should read --1-nitroso-2,6-dimethylpiperidine--.

Signed and Sealed this

Thirteenth Day of May, 1997

Attest:

BRUCE LEHMAN

Attesting Officer    Commissioner of Patents and Trademarks